United States Patent
Chen et al.

(10) Patent No.: US 12,317,930 B2
(45) Date of Patent: Jun. 3, 2025

(54) ATOMIZING CORE AND ATOMIZER

(71) Applicants: LUXSHARE PRECISION INDUSTRY COMPANY LIMITED, Shenzhen (CN); ZhiYing Chen, Shenzhen (CN)

(72) Inventors: ZhiYing Chen, Shenzhen (CN); HuaBing Li, Shenzhen (CN); Lei He, Shenzhen (CN)

(73) Assignees: LUXSHARE PRECISION INDUSTRY COMPANY, LIMITED, Shenzhen (CN); Zhiying Chen, Shenzhen (CN)

( * ) Notice: Subject to any disclaimer, the term of this patent is extended or adjusted under 35 U.S.C. 154(b) by 438 days.

(21) Appl. No.: 17/982,781

(22) Filed: Nov. 8, 2022

(65) Prior Publication Data
US 2023/0180835 A1 Jun. 15, 2023

(30) Foreign Application Priority Data
Nov. 11, 2021 (CN) .............................. 202111330499

(51) Int. Cl.
*A24F 40/46* (2020.01)
*A24F 40/10* (2020.01)
(Continued)

(52) U.S. Cl.
CPC .............. *A24F 40/46* (2020.01); *A24F 40/10* (2020.01); *A24F 40/44* (2020.01); *H05B 3/46* (2013.01); *H05B 2203/021* (2013.01)

(58) Field of Classification Search
CPC .......... A24F 40/10; A24F 40/46; A24F 40/44; H05B 3/46
See application file for complete search history.

(56) References Cited

U.S. PATENT DOCUMENTS

| | | | |
|---|---|---|---|
| 2015/0090280 A1 | 4/2015 | Chen | |
| 2016/0000146 A1* | 1/2016 | Zhu | A24F 40/46 392/404 |

(Continued)

FOREIGN PATENT DOCUMENTS

| | | |
|---|---|---|
| CN | 105266204 A | 1/2016 |
| CN | 105310114 A | 2/2016 |

(Continued)

OTHER PUBLICATIONS

"Tabish et al., A facile synthesis of porous graphene for efficient water and wastewater treatment, 2018, Scientific Reports 8, p. 1-14" (Year: 2018).*

*Primary Examiner* — Philip Y Louie
*Assistant Examiner* — Timothey Tuan-Kha Tran
(74) *Attorney, Agent, or Firm* — Birch, Stewart, Kolasch & Birch, LLP

(57) ABSTRACT

The present disclosure provides an atomizing core and an atomizer. The atomizing core includes a core member, a heating member, a guiding member, and a porous graphene adsorption member. The heating member is disposed on the core member. The guiding member is disposed on the core member and is in fluid communication with an opening of the atomizer. The porous graphene adsorption member is disposed on the heating member. Specifically, porous graphene is a porous material, and the adsorption effect of filler may be improved by the excellent porous properties of porous graphene. In addition, porous graphene is also a self-sterilizing material, which not only improves the filtering effect of the filler but may even make the filtering effect reach medical grade. Most importantly, the problem of dry burning may be avoided by the high melting point of porous graphene, therefore the product safety is greatly improved.

20 Claims, 3 Drawing Sheets

(51) Int. Cl.
    *A24F 40/44*     (2020.01)
    *H05B 3/46*     (2006.01)

(56) References Cited

U.S. PATENT DOCUMENTS

| | | | |
|---|---|---|---|
| 2016/0000149 | A1 | 1/2016 | Scatterday |
| 2018/0279672 | A1 | 10/2018 | Davis et al. |
| 2020/0268051 | A1 | 8/2020 | Davis et al. |
| 2020/0352256 | A1 | 11/2020 | Hejazi et al. |
| 2021/0321671 | A1 * | 10/2021 | Chen ................ A24F 40/46 |

FOREIGN PATENT DOCUMENTS

| | | |
|---|---|---|
| CN | 106418715 A | 2/2017 |
| CN | 109744583 A | 5/2019 |
| CN | 210382630 U | 4/2020 |
| CN | 112043011 A | 12/2020 |
| CN | 112545066 A | 3/2021 |
| CN | 112914163 A | 6/2021 |
| EP | 2 992 768 A1 | 3/2016 |
| EP | 3 199 042 A1 | 8/2017 |
| JP | 2019-122372 A | 7/2019 |
| JP | 2019-521664 A | 8/2019 |
| JP | 2019-193641 A | 11/2019 |
| JP | 2021-505128 A | 2/2021 |
| WO | WO 2021/098292 A1 | 5/2021 |
| WO | WO 2021/168958 A1 | 9/2021 |

* cited by examiner

ATOMIZING CORE AND ATOMIZER

CROSS REFERENCE TO RELATED DISCLOSURE

This application claims the priority benefit of China Patent Application Number 202111330499.9, filed on Nov. 11, 2021, the full disclosure of which is incorporated herein by reference.

BACKGROUND

Technical Field

The present disclosure is related to atomizing equipment, and in particular, an atomizing core and an atomizer.

Related Art

In the prior art, atomizing equipment is used to atomize specific fillers for use by users. For example, the atomizing equipment may be an electronic cigarette. An electronic cigarette is an electronic device that simulates a traditional cigarette. The electronic cigarette is composed of a heating member, a silo, and a battery. With the power provided by the battery, the heating member can atomize the filler in the silo to simulate the smoke of traditional cigarettes.

In order to allow the filler to be continuously supplied to the heating member, cotton is generally disposed between the heating member and the filler in the silo, so that the filler is adsorbed and guided to flow by the capillary action of the cotton. However, cotton may not be used for a long time because the adsorption capacity of cotton is poor. In addition, using cotton to filter fillers may generate filler residues. Filler residues may significantly degrade smoke quality, resulting in a degraded user experience. The most important thing is that when the amount of filler is insufficient, the cotton with a low melting point is not only easy to scorch, but also more likely to catch fire and cause danger. Therefore, how to provide a safe, stable, and good quality filter element has become an urgent issue to be solved in the art.

SUMMARY

The embodiments of the present disclosure disclose an atomizing core and an atomizer, in order to solve the problem that the prior art atomizing core including cotton causes a poor adsorption effect and may even cause harm.

In order to solve the above technical problems, the present disclosure is implemented as follows.

First, an atomizing core is provided, which includes a core member, a heating member, a guiding member, and a porous graphene adsorption member. The heating member is disposed on the core member. The guiding member is disposed on the core member and is in fluid communication with an opening of the atomizer. The porous graphene adsorption member is disposed on the heating member.

In some embodiments, a porosity of the porous graphene adsorption member is greater than 80%.

In some embodiments, the core member and the porous graphene adsorption member are cylindrical, and the porous graphene adsorption member is sleeved on the heating member and the core member.

In some embodiments, the core member has a guiding space, and the guiding member is in fluid communication with the guiding space.

In some embodiments, the heating member is a heating coil, and the heating coil is disposed to surround the core member.

In some embodiments, the atomizing core further includes a wire electrically connected to the heating member and a power supply of the atomizer.

In some embodiments, the atomizing core further includes a porous case. Wherein the porous case is sleeved on the porous graphene adsorption member, and the porous case covers the core member, the heating member, and the porous graphene adsorption member and part of the guiding member.

In some embodiments, a material of the porous case is polypropylene or polytetrafluoroethylene.

In some embodiments, the heating member surrounds and is in contact with an outer surface of the core member. The porous graphene adsorption member surrounds and is in contact with an outer surface of the core member and the heating member. The porous case surrounds and is in contact with an outer surface of the porous graphene adsorption member.

In some embodiments, the core member is a porous plastic member.

Second, an atomizer is provided, which includes an atomizer body and the atomizing core mentioned above. The atomizing core is disposed in the atomizer body.

In some embodiments, the atomizer further includes a silo disposed in the atomizer body. Wherein the atomizing core is disposed in the silo, and a filler is stored between the silo and the atomizing core.

The present disclosure uses porous graphene to adsorb and filter the filler to replace the cotton filter element in the prior art. Specifically, porous graphene is a porous material, and the adsorption of fillers may be improved by excellent porous properties of the porous graphene. In addition, porous graphene is also a self-sterilizing material, which not only improves the filtering effect of the filler but may even make the filtering effect reach medical grade. Therefore, the atomizer may be applied to medical-grade products by filtering the filler through porous graphene. Most importantly, the problem of dry burning may be avoided by the high melting point of porous graphene, therefore the product safety is greatly improved. Thus, the present disclosure achieves a filter element that is safe, stable, and with good quality.

BRIEF DESCRIPTION OF THE DRAWINGS

The figures described herein are used to provide a further understanding of the present disclosure and constitute a part of the present disclosure. The exemplary embodiments and descriptions of the present disclosure are used to illustrate the present disclosure and do not limit the present disclosure, in which.

DETAILED DESCRIPTION OF THE EMBODIMENTS

In order to make the objectives, technical solutions, and advantages of the present disclosure clearer, the technical solutions of the present disclosure will be described clearly and completely in conjunction with specific embodiments and the figures of the present disclosure. Obviously, the described embodiments are only a part of the embodiments of the present disclosure, rather than all the embodiments. Based on the embodiments in the present disclosure, all other embodiments obtained by a person of ordinary skill in the art without creative work fall within the protection scope of this disclosure.

The following description is of the best-contemplated mode of carrying out the present disclosure. This description is made for the purpose of illustrating the general principles of the present disclosure and should not be taken in a limiting sense. The scope of the present disclosure is best determined by reference to the appended claims.

Figure 1:
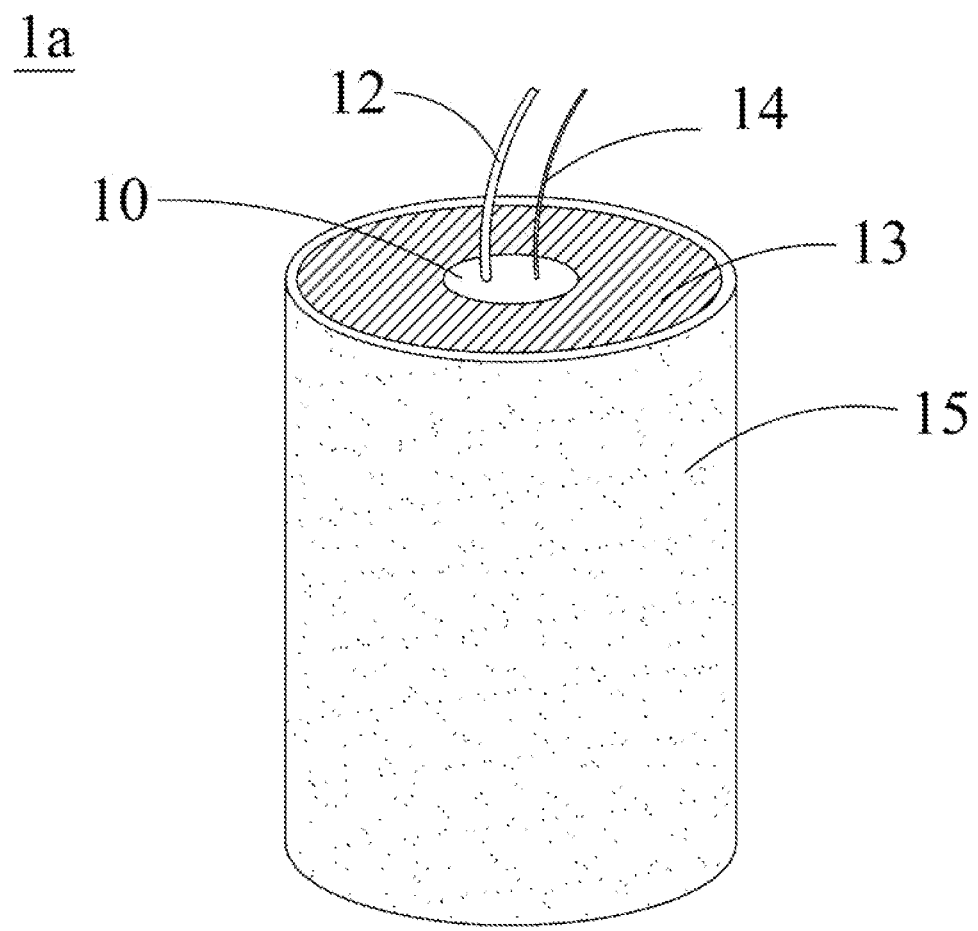
FIG. 1 is a schematic diagram of the atomizing core of the atomizer according to an embodiment of the present disclosure.
Figure 2:
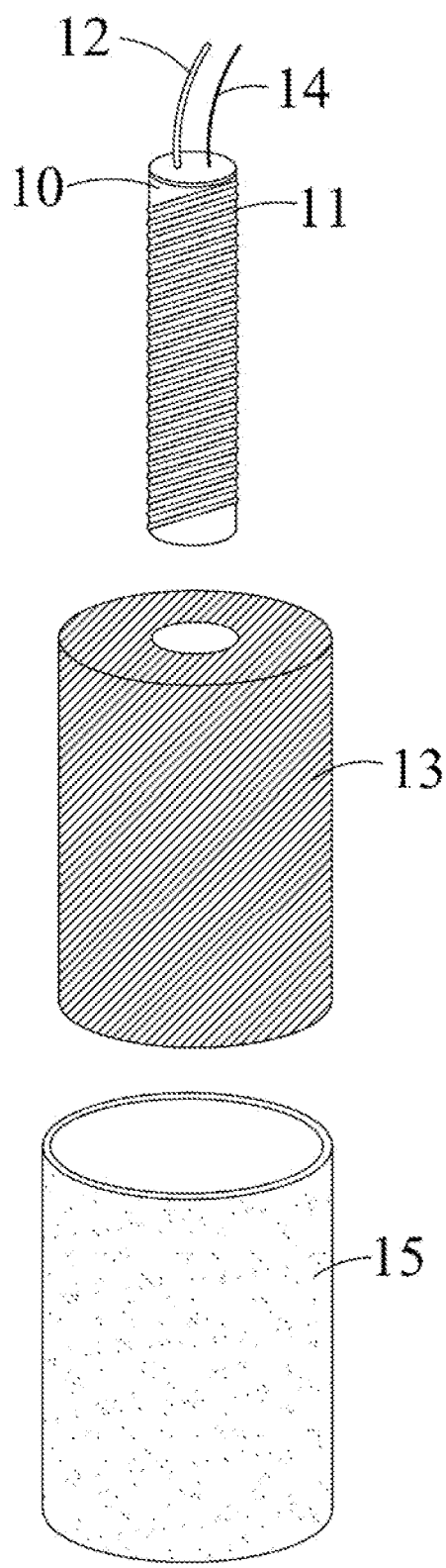
FIG. 2 is an exploded view of the atomizing core of the atomizer according to an embodiment of the present disclosure.

FIG. 1 and FIG. 2 respectively are a schematic diagram and an exploded view of the atomizing core of the atomizer according to an embodiment of the present disclosure. As shown in the figure, the atomizing core 1a of the atomizer 1 includes a core member 10, a heating member 11, a guiding member 12, and a porous graphene adsorption member 13. The heating member 11 is disposed on the core member 10. The guiding member 12 is disposed on the core member 10 and is in fluid communication with an opening of the atomizer 1. The porous graphene adsorption member 13 is disposed on the heating member 11. In some embodiments, the atomizing core 1a is disposed in the silo of the atomizer 1 and used to adsorb the filler in the silo. For example, the porous graphene adsorption member 13 has high adsorption due to the porous structure thereof, and the porous graphene adsorption member 13 may adsorb the filler from the silo. The adsorbed filler flows to the heating member 11 through the porous graphene adsorption member 13 and is heated by the heating member 11. After being heated by the heating member 11, the filler is formed into a mixture of liquid particles and gas (i.e., atomized). Finally, the atomized filler flows through the core member 10 and the guiding member 12 in sequence to the opening of the atomizer 1 for the user to inhale.

In some embodiments, the core member 10 is made of a porous material as porous plastic, but the present disclosure is not limited thereto. In some embodiments, the material of the core member 10 may be heat-resistant plastic. More specifically, "heat-resistant" herein refers to having the property of being able to withstand 100 degrees Celsius without thermal cracking and thermal deformation. Preferably, "heat-resistant" refers to having the property of being able to withstand 150 degrees Celsius without thermal cracking and thermal deformation. Since the core member 10 is required to carry the heating member 11 for heating the filler, the core member 10 is required to be made of materials that may withstand high temperatures. In some embodiments, the heat-resistant plastic may be one of polypropylene, modified polystyrene, polytetrafluoroethylene, polyimide, modified polyphenylene ether, polyphenylene sulfide, and polyether ether ketone, but the present disclosure is not limited thereto. That is, all heat-resistant plastics known by a person having ordinary skill in the art may be used in the present disclosure. In some embodiments, the material of the core member 10 is porous ceramic or metal, but the present disclosure is not limited thereto.

In some embodiments, the core member 10 has a guiding space therein, and the guiding member 12 is in fluid communication with the guiding space. For example, the core member 10 may be a hollow cylinder, and the filler outside the core member 10 may flow into the guiding space inside the core member 10 through the pores on the surface of the core member 10. Furthermore, the filler flowing into the guiding space may flow out of the atomizer 1 through the guiding member 12. It should be noted that the cylindrical shape shown in FIG. 1 is only an example, and the shape of the core member 10 of the present disclosure is not limited thereto. For example, the core member 10 may be a hollow elliptical cylinder, a hollow quadrangular cylinder, a hollow pentagonal cylinder, or a hollow special-shaped cylinder. By disposing the core member 10 in different shapes, the core member 10 and the atomizing core 1a including the core member 10 may be used in atomizers 1 with different shapes and sizes.

In some embodiments, the porosity of the core member 10 is greater than 50%. For example, the porosity of the core member 10 may be 50%, 55%, 60%, 65%, 75%, 80%, or any range between the values mentioned above. The properties such as velocity and pressure during the flow of the filler may be effectively adjusted by disposing different porosity, thereby expanding the scope of application.

In some embodiments, the pores in the core member 10 may have the same size and shape, so that the filler (whether liquid or gaseous) passing through the pores may have a similar size, therefore a stable and uniform atomized filler is provided. However, the present disclosure is not limited thereto. In other embodiments, the pores of the core member 10 may also have different sizes and shapes, so that the fillers passing through the pores may have various sizes. Therefore, atomized filler with a complex taste is generated.

In some embodiments, the heating member 11 is a heating coil, and the heating coil is disposed to surround the core member 10. Specifically, the heating coil may surround the core member 10 with a specific slope like a thread. Wherein, the distance of the heating coils of two adjacent turns may be adjusted according to the requirement. For example, when stable heating is required, the distance between the heating coils of two adjacent turns may be small to avoid temperature gradients between the heating coils of the two adjacent turns. On the other hand, the distance between the heating coils of two adjacent turns may be larger in order to avoid heating too fast. In addition, the thickness of the heating coil may also be adjusted according to the requirement. For example, when the coil diameter of the heating coil is larger, the resistance of the heating coil is smaller. So that the heat generated when the current passes through is smaller. On the other hand, when the coil diameter of the heating coil is smaller, the resistance of the heating coil is larger. So that the heat generated when the current passes through is larger. Therefore, the thickness of the heating coil may be adjusted according to heating speed.

In some embodiments, the material of the heating coil may include copper, aluminum, molybdenum, tungsten, gold, chromium, nickel, platinum, titanium, iridium, rhodium, or other metal materials with good electrical conductivity, or any combination thereof. For example, the heating coil may be an alloy, and a better heating effect may be achieved by adjusting the composition ratio of the alloy.

In some embodiments, the porous graphene adsorption member 13 may be the same cylindrical shape as the core member 10, and the porous graphene adsorption member 13 is sleeved on the heating member 11 and the core member 10. That is, the shape of the porous graphene adsorption member 13 may correspond to the shape of the core member 10. However, the present disclosure is not limited thereto. In other embodiments, the shape of the core member 10 may not correspond to the shape of the porous graphene adsorption member 13. For example, the shape of the core member 10 may be cylindrical, and the porous graphene adsorption member 13 may be spherical.

In some embodiments, the porous graphene adsorption member 13 is formed by one of a photoetching process, a carbothermic reduction process, a wet etching process, a template process, a solvothermal process, and a chemical vapor deposition process. For example, carbon atoms may be bombarded out of the graphene lattice by bombarding the graphene with high-energy electron, ion, or photon beams (ie, a photoetching process). Alternatively, porous graphene may be obtained by using carbon atoms of graphene as a reducing agent to reduce metal oxides to form vacancies on the graphene (i.e., a carbothermic reduction process).

Furthermore, the porous graphene formed by the processes mentioned above is a material with extremely high formability. That is, the porous graphene adsorption member 13 may be formed into various shapes according to design requirements, so as to match the atomizer 1 products of various shapes. In addition, the porous graphene is not only non-toxic and harmless to the human body but also has effective antibacterial due to the material properties of porous graphene. Therefore, the atomizing core 1a including porous graphene of the present disclosure may be applied in the field of various atomizing devices without being harmful to humans. Most importantly, porous graphene is a high-temperature-resistant material. Compared with cotton in the prior art, porous graphene may maintain stable operation when the filler is reduced without drying out or even catching fire. In this way, the safety of users is greatly improved.

In some embodiments, the porosity of porous graphene adsorption member 13 is greater than 80%. For example, the porosity of the porous graphene adsorption member 13 may be 80%, 82.5%, 85%, 87.5%, 90%, or any range between the values mentioned above. Similar to core member 10, the properties such as velocity and pressure during the flow of the filler may be effectively adjusted by disposing different porosity, thereby expanding the scope of application.

In some embodiments, the atomizing core 1a of the atomizer 1 further includes a wire 14 electrically connected to the heating member 11 and the power supply of the atomizer 1. For example, the material of the wire 14 may include copper, aluminum, molybdenum, tungsten, gold, chromium, nickel, platinum, titanium, iridium, rhodium, or other metal materials with good electrical conductivity, or any combination thereof. In other embodiments, the material of the wire 14 may also be a non-metallic material, as long as the material used has good conductivity. Preferably, the material of the wire 14 may be the same as that of the heating coil, so as to reduce the difference in resistance value between the interfaces of the two materials.

In some embodiments, the atomizing core 1a of the atomizer 1 further includes a porous case 15. The porous case 15 is sleeved on the porous graphene adsorption member 13, and the porous case 15 covers the core member 10, the heating member 11, the porous graphene adsorption member 13, and part of guiding member 12. Similar to the core member 10, the preferred material of the porous case may also be heat-resistant plastic, and "heat-resistant" refers to having the property of being able to withstand 100 degrees Celsius without thermal cracking and thermal deformation. For example, the material of the porous case 15 is polypropylene or PTFE, but the present disclosure is not limited thereto.

In some embodiments, the heating member 11 surrounds and is in contact with the outer surface of the core member 10. The porous graphene adsorption member 13 surrounds and is in contact with the outer surface of the core member 10 and the heating member 11. The porous case 15 surrounds and is in contact with the outer surface of the porous graphene adsorption member 13. The heating member 11 is between the porous graphene adsorption member 13 and the core member 10. The porous graphene adsorption member 13 is between the porous case 15, the porous graphene adsorption member 13, and the heating member 11.

In some embodiments, the porosity of the porous case 15 is greater than or equal to 50%. For example, the porosity of porous case 15 may be 50%, 55%, 60%, 65%, 70%, 75%, 80%, or any range between the values mentioned above. The properties such as velocity and pressure during the flow of the filler may be effectively adjusted by disposing different porosity, thereby expanding the scope of application.

Figure 3:
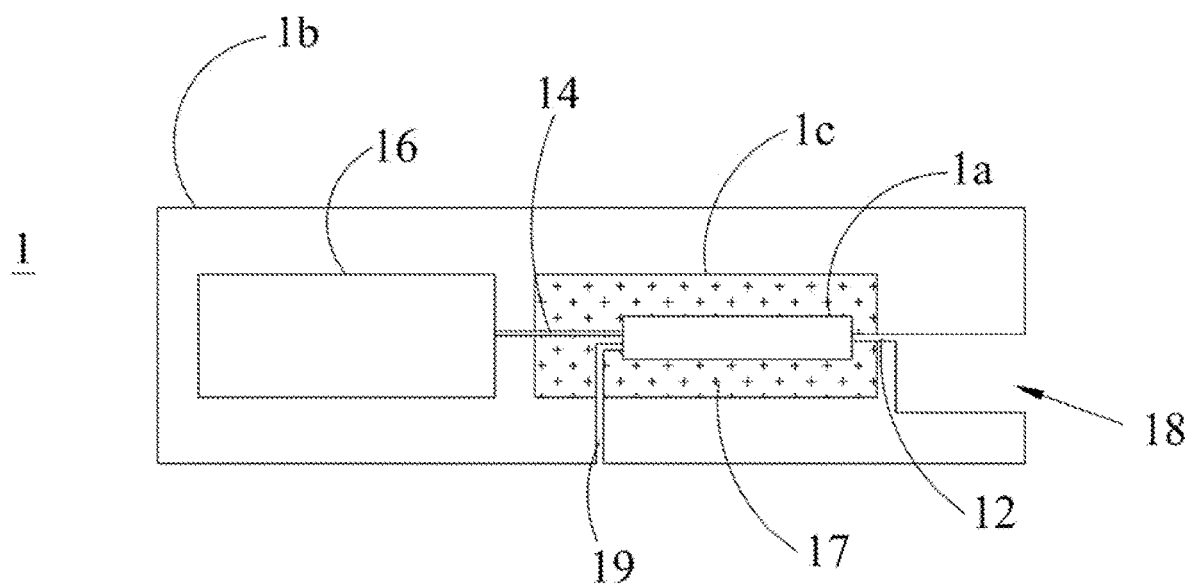
FIG. 3 is a schematic diagram of the atomizer according to an embodiment of the present disclosure.

FIG. 3 is a schematic diagram of the atomizer according to an embodiment of the disclosure. As shown in the figure, the atomizer 1 includes an atomizer body 1b and an atomizing core 1a mentioned above. The atomizing core 1a is disposed in the atomizer body 1b. More specifically, the atomizer 1 further includes a silo 1c disposed in the atomizer body 1b. The atomizing core 1a is disposed in the silo 1c, and a filler 17 is stored between the silo 1c and the atomizing core 1a. For example, when the atomizer 1 mentioned above is an electronic cigarette, the silo 1c may be the "vape cartridge" of the electronic cigarette, and the filler 17 may be the "e-liquid" of the electronic cigarette. Wherein, the battery 16 in the atomizer body 1b provides power to the heating member 11 through the wire 14. Then, the porous case 15 adsorbs the e-liquid in the silo by the porous structure, and the porous graphene adsorption member 13 adsorbs the e-liquid passing through the porous case 15 by the porous structure. In some embodiments, the core member 10 also adsorbs the e-liquid by the porous structure. Wherein, the e-liquid in silo 1c is heated by heating member 11 into atomized e-liquid during the process of sequentially passing through the porous case 15, the porous graphene adsorption member 13, and the core member 10 in the atomizing core 1a. Finally, the atomized e-liquid enters the user's mouth along with the guiding space, the guiding member 12, the opening 18, or a suction nozzle of the atomizer 1 through the user's suction. In some embodiments, the silo 1c may be a medical atomizer, and the filler may be a liquid medicine. The liquid medicine in silo 1c is heated by the heating member 11 into a mist during the process of sequentially passing through the porous case 15, the porous graphene adsorption member 13, and the core member 10 in the atomizing core 1a. Finally, the medicinal mist enters the user's mouth or nasal cavity along with the guiding space, the guiding member 12, the opening 18, or the suction nozzle of the atomizer 1 by the user's suction.

In some embodiments, the porous structure of the porous graphene adsorption member 13 may adsorb e-liquid or liquid medicine from the silo 1c. The porous structure of the porous graphene adsorption member 13 has oil-conducting or liquid-conducting properties. The adsorbed e-liquid or medicine absorbed is evenly guided around the core member 10 by the porous structure of the porous graphene adsorption member 13, so that the e-liquid or medicine may be uniformly heated and atomized by the heating member 11. In some embodiments, the porous graphene adsorption member 13 also has filtering performance based on dense porous structure thereof, so that the adsorbed e-liquid or medicine may also be filtered by the porous graphene adsorption member 13 when passing through the porous graphene adsorption member 13.

In some embodiments, the atomizer 1 further includes an air inlet channel 19 penetrated through the atomizer body 1b. The air inlet channel 19 is in fluid communication with the atomizing core 1a. The outside air may enter the atomizing core 1a through the air inlet channel 19 and mix with the atomized filler, thereby producing a low-concentration atomized filler suitable for consumption.

In summary, the present disclosure uses porous graphene to adsorb and filter the filler to replace the cotton filter element in the prior art. Specifically, porous graphene is a porous material, and the adsorption of fillers may be improved by excellent porous properties of the porous graphene. In addition, porous graphene is also a self-sterilizing material, which not only improves the filtering effect of the filler but may even make the filtering effect reach medical grade. Therefore, the atomizer may be applied to medical-grade products by filtering the filler through porous graphene. Most importantly, the problem of dry burning may be avoided by the high melting point of porous graphene, therefore the product safety is greatly improved. Thus, the present disclosure achieves a filter element that is safe, stable, and with good quality.

Although the present disclosure has been explained in relation to its preferred embodiment, it does not intend to limit the present disclosure. It will be apparent to those skilled in the art having regard to this present disclosure that other modifications of the exemplary embodiments beyond those embodiments specifically described here may be made without departing from the spirit of the invention. Accordingly, such modifications are considered within the scope of the invention as limited solely by the appended claims.

What is claimed is:

1. An atomizing core of an atomizer, comprising:
   a core member;
   a heating member disposed on the core member;
   a guiding member disposed on the core member, wherein the guiding member is in fluid communication with an opening of the atomizer; and
   a porous graphene adsorption member disposed on the heating member.

2. The atomizing core of the atomizer of claim 1, wherein a porosity of the porous graphene adsorption member is greater than 80%.

3. The atomizing core of the atomizer of claim 1, wherein the core member and the porous graphene adsorption member are cylindrical, and the porous graphene adsorption member is sleeved on the heating member and the core member.

4. The atomizing core of the atomizer of claim 1, wherein the core member has a guiding space, and the guiding member is in fluid communication with the guiding space.

5. The atomizing core of the atomizer of claim 1, wherein the heating member is a heating coil, and the heating coil is disposed to surround the core member.

6. The atomizing core of the atomizer of claim 1, further comprising a wire electrically connected to the heating member and a power supply of the atomizer.

7. The atomizing core of the atomizer according to claim 1, further comprising a porous case, wherein the porous case is sleeved on the porous graphene adsorption member, and the porous case covers the core member, the heating member, the porous graphene adsorption member, and at least a part of the guiding member.

8. The atomizing core of the atomizer of claim 7, wherein a material of the porous case is polypropylene or polytetrafluoroethylene.

9. The atomizing core of the atomizer of claim 7, wherein the heating member surrounds and is in contact with an outer surface of the core member, the porous graphene adsorption member surrounds and is in contact with the outer surface of the core member and the heating member, and the porous case surrounds and is in contact with an outer surface of the porous graphene adsorption member.

10. The atomizing core of the atomizer of claim 1, wherein the core member is a porous plastic member.

11. An atomizer, comprising:
    an atomizer body; and
    an atomizing core comprising:
      a core member;
      a heating member disposed on the core member;
      a guiding member disposed on the core member, wherein the guiding member is in fluid communication with an opening of the atomizer; and
      a porous graphene adsorption member disposed on the heating member,
    wherein the atomizing core is disposed in the atomizer body.

12. The atomizer of claim 11, further comprising a silo disposed in the atomizer body, wherein the atomizing core is disposed in the silo, and a filler is stored between the silo and the atomizing core.

13. The atomizer of claim 11, wherein a porosity of the porous graphene adsorption member is greater than 80%.

14. The atomizer of claim 11, wherein the core member and the porous graphene adsorption member are cylindrical, and the porous graphene adsorption member is sleeved on the heating member and the core member.

15. The atomizer of claim 11, wherein the core member has a guiding space, and the guiding member is in fluid communication with the guiding space.

16. The atomizer of claim 11, wherein the heating member is a heating coil, and the heating coil is disposed to surround the core member.

17. The atomizer of claim 11, further comprising a wire electrically connected to the heating member and a power supply of the atomizer.

18. The atomizer according to claim 11, further comprising a porous case, wherein the porous case is sleeved on the porous graphene adsorption member, and the porous case covers the core member, the heating member, the porous graphene adsorption member, and at least a part of the guiding member.

19. The atomizer of claim 18, wherein a material of the porous case is polypropylene or polytetrafluoroethylene.

20. The atomizer of claim 18, wherein the heating member surrounds and is in contact with an outer surface of the core member, the porous graphene adsorption member surrounds and is in contact with the outer surface of the core member and the heating member, and the porous case surrounds and is in contact with an outer surface of the porous graphene adsorption member.

* * * * *